US00PP28168P3

(12) United States Plant Patent
Olesen

(10) Patent No.: US PP28,168 P3
(45) Date of Patent: Jul. 11, 2017

(54) COMPACT FLORIBUNDA ROSE PLANT NAMED 'POULPAL062'

(50) Latin Name: ***Rosa* hybrid**
Varietal Denomination: Poulpal062

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 12 days.

(21) Appl. No.: 14/756,268

(22) Filed: Aug. 20, 2015

(65) Prior Publication Data

US 2017/0055404 P1 Feb. 23, 2017

(51) Int. Cl.
*A01H 5/02* (2006.01)

(52) U.S. Cl.
USPC ..... Plt./150

(58) Field of Classification Search
USPC ..... Plt./141, 150
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, medium red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal062'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2006 and the resulting seeds were planted in a controlled environment in Fredensborg, Denmark. The new variety, named 'Poulpal062', originated as a single seedling from the stated cross.

The new variety may be distinguished from its male pollen parent and female seed parent primarily by the following characteristics. The male pollen parent and the female seed parent have flowers which are Red Group 40A while the new variety has flowers which are Red Group 40C.

The objective of the hybridization of this rose variety was to create a new and distinct variety for garden use with unique qualities, such as:

1. Uniform and abundant medium red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal062' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpal062' was selected in the spring of 2007 by the inventor as a single plant from the progeny of the aforementioned hybridization.

Asexual reproduction of 'Poulpal062' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpal062' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal062'.

Specifically illustrated in FIG. 1 of the drawings are open flowers, petals detached, sepals detached, flower buds, and reproductive flower parts.

Figure 1:
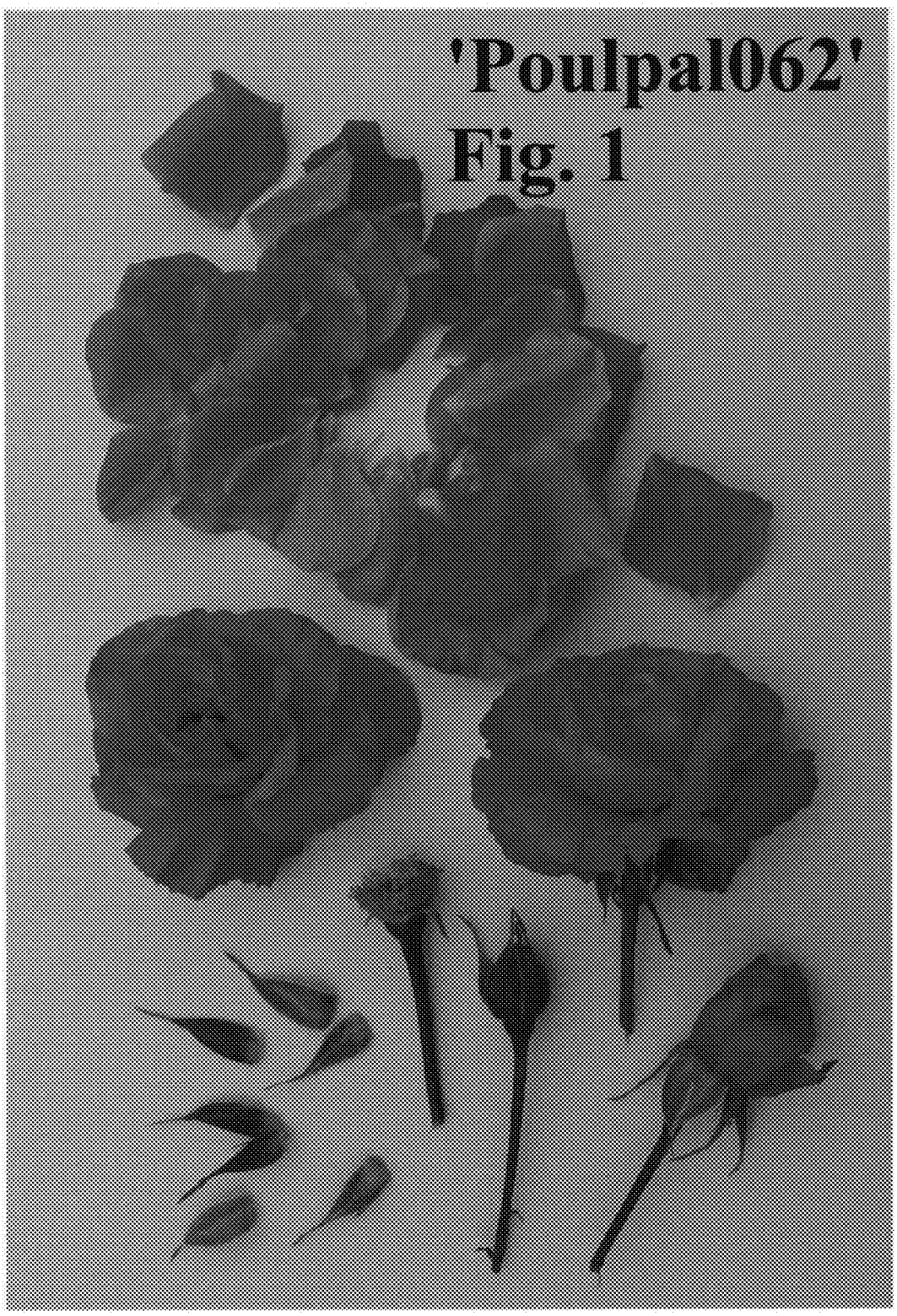
Figure 2:
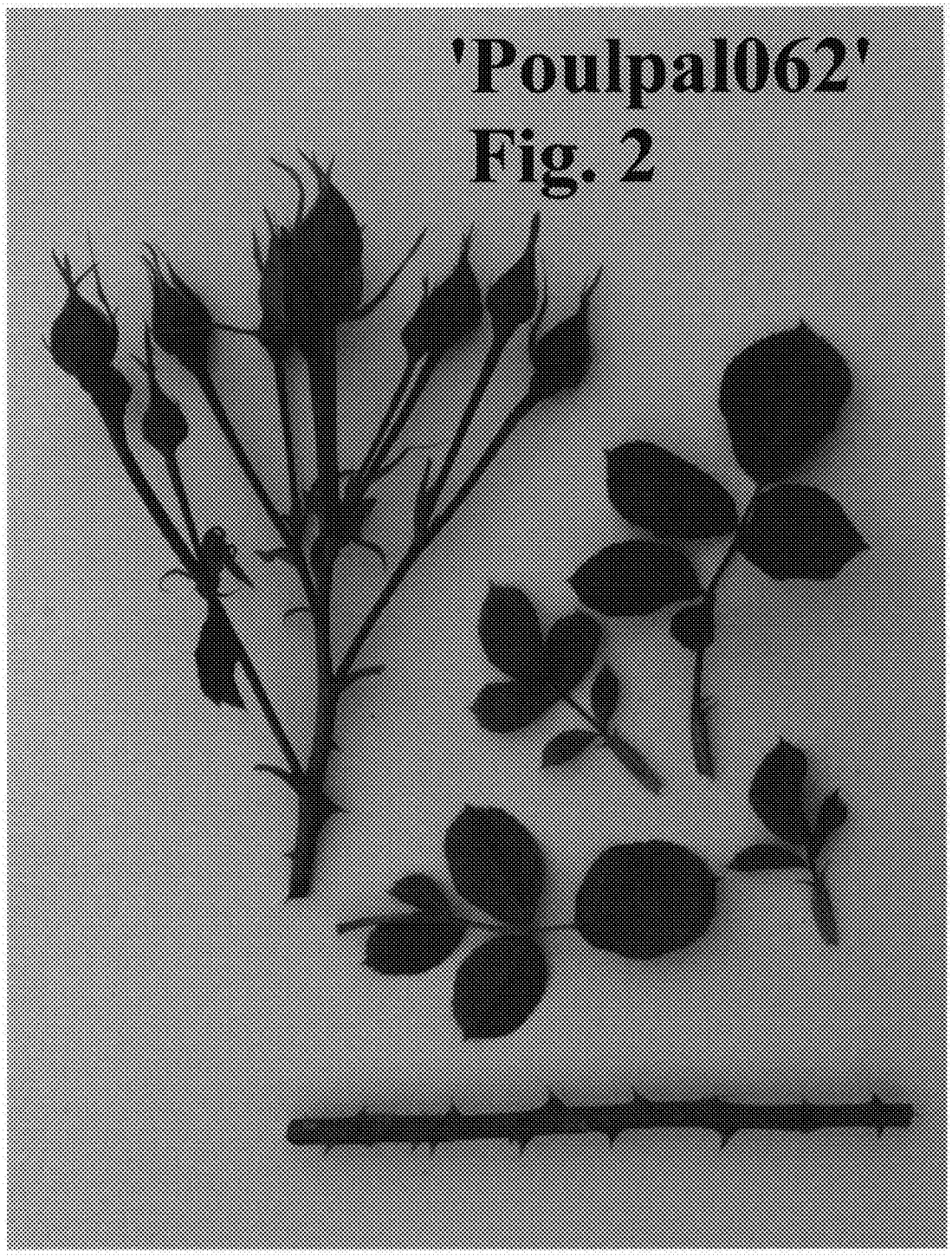

Specifically illustrated in FIG. 2 of the drawings are juvenile and mature leaves, bare stem, and a cluster of unopened flower buds on a flowering branch. Plants shown are 2 years of age.

DETAILED DESCRIPTION OF THE VARIETY

The following is a description of 'Poulpal062', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulac011', U.S. Plant Pat. No. 15,821 are compared to 'Poulpal062' in Chart 1.

CHART 1

| | 'Poulpal062' | 'Poulac011' |
|---|---|---|
| Petal Count | 50 petals | 40 to 45 petals |
| Flower Diameter | 75 mm | 50 mm |
| General Tonality of Flower Color | Red Group 40C becoming Red Group 43C as flowers mature | Red Group 52A to 52B with light intonations of Red-Purple Group 67B |

FLOWER AND FLOWER BUD

Blooming habit: Continuous.

Flower bud:

*Size.*—Upon opening, 23 mm in length from base of receptacle to end of bud. Bud diameter is 15 mm.

*Bud form.*—Ovoid.

*Bud color.*—As sepals divide petals are Red Group 41A.

*Sepal inner surface.*—Color: Yellow-Green Group 147D with intonations of Greyed-Brown Group 199C. Surface: Lightly pubescent.

*Sepal outer surface.*—Color: Yellow-Green Group 144A with intonations of Red-Purple Group 183A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—33 mm long, 10 mm wide.

*Receptacle.*—Texture: Smooth. Size: 6 mm in height, 6 mm wide. Color: Yellow-Green Group 144A with intonations of Red-Purple Group 183A. Shape: Campanulate.

*Pedicel.*—Surface: Smooth. Length: 30 mm. Diameter: 3 mm on average. Color: Yellow-Green Group 144A with intonations of Greyed-Purple Group 184A. Strength: Strong.

*Peduncle.*—Length: 3 to 7 cm. Diameter: About 3 mm. Color: Yellow-Green Group 145A. Texture: Smooth.

Flower bud development: Flower buds are borne in panicles of about 15 flower buds per stem. Panicles are about 20 cm in diameter.

Flower bloom:

*Fragrance.*—Light floral scent.

*Duration.*—The blooms have a duration on the plant of approximately 12 days. Petals fall cleanly away from plant after flowers have fully matured.

*Size.*—Flower diameter is 75 mm when open. Flower depth is 30 mm.

*Flower shape.*—Quartered-rosette, very double, with many overlapping petals packed into quarter sections.

*Shape of flower, side view.*—The upper portion is flattened convex. The lower portion is concave.

Petalage: Under normal conditions, flowers have 50 petals total, 6 to 9 of which are petaloids.

General tonality of flower: Open flowers are Red Group 40C becoming Red Group 43C as flowers fully mature.

Petal color:

*Upon opening, outer and inner petals.*—Upper surface: Red Group 40B with occasional streaks of White Group 155B. Lower surface: Red Group 40C.

*Basal petal spots, upon opening.*—Upper surface: Yellow Group 4A. Lower surface: Yellow Group 4A.

*After opening, inner and outer petals.*—Upper surface: Red Group 43C with occasional streaks of White Group 155B. Lower surface: Red Group 43D.

*Basal petal spots, after opening.*—Upper surface: Yellow Group 4A. Lower surface: Yellow Group 4A.

Petals:

*Petal reflex.*—Slightly reflexed.

*Margin.*—Entire and uniform. Strong undulations.

*Shape.*—Generally broadly elliptical. Apex shape: Rounded. Base shape: Acute.

*Size.*—30 mm (l)×30 mm (w).

*Texture.*—Smooth.

*Thickness.*—Average.

Petaloids:

*Size.*—25 mm (l) by 15 mm (w).

*Quantity.*—6 to 9.

*Shape.*—Asymmetric, with an oblique base and rounded apex.

*Color.*—Upper surface is Red Group 43C with occasional streaks of White Group 155B. Lower surface is Red Group 43D. Basal zone is Yellow Group 4A above and underneath.

Reproductive flower parts:

*Pollen.*—None observed.

*Anthers.*—Size: 2 mm in length. Color: Yellow Group 11C. Quantity: 55 on average.

*Filaments.*—Color: Yellow Group 12B. Length: 4 mm.

*Pistils.*—Length: 8 mm. Quantity: 30 on average.

*Stigmas.*—Color: Green-White Group 157A.

*Styles.*—Color: White Group 155A.

*Location of stigmas.*—Superior in location relative to the length of the filaments and the height of the anthers.

*Hips.*—None observed to date.

PLANT

Plant growth: Upright, bushy. Plants are 50 cm in height, and 45 cm wide.

Stems:

*Color.*—Juvenile growth: Yellow-Green Group 144B. Mature growth: Yellow-Green Group 144A.

*Length.*—On average, canes are 20 cm from the base of the plant to the flowering portion.

*Diameter.*—5 mm.

*Internodes.*—On mature canes about 25 mm between nodes.

*Surface texture.*—Young wood: Smooth. Older wood: Smooth.

Long prickles:

*Incidence.*—15 prickles per 10 cm of stem.

*Size.*—Average length of prickles on mature stems is 6 mm.

*Shape.*—Upper portion is linear. Lower portion is concave.

*Color.*—Juvenile prickles: Greyed-Red Group 179B. Mature prickles: Greyed-Yellow Group 162B.

Plant foliage:

*Compound leaf.*—120 mm (l)×80 (w).

*Quantity.*—3 leaves per 10 cm of stem on average.

*Color of juvenile foliage.*—Upper side: Yellow-Green Group 144A. Lower side: Yellow-Green Group 144B. Anthocyanin: Greyed-Orange Group 176A.

*Color of mature foliage.*—Upper side: Yellow-Green Group 147A. Lower side: Yellow-Green Group 147B.

Plant leaves and leaflets:

*Stipules.*—Size: 25 mm long, 9 mm wide. Quantity: 2 per compound leaf. Shape: Linear, slightly broad based with outward extending apices. Margins: Finely serrated. Color: Yellow-Green Group 144A.

*Petiole.*—Length: 30 mm. Diameter: 1.5 mm.

*Upper surface.*—Color: Yellow-Green Group 144A.

*Lower surface.*—Color: Yellow-Green Group 144A.

*Rachis.*—Length: 40 mm. Upper surface: Color: Yellow-Green Group 144A.

*Lower surface.*—Color: Yellow-Green Group 144A.

*Leaflet.*—Quantity: Normally 5 or 7 leaflets. Margins: Serrated.

*Size.*—On average terminal leaflets are 40 mm long, 35 mm wide.

*Shape.*—Generally ovate. Base: Rounded. Apex: Cuspidate.

*Texture.*—Smooth.

*Thickness.*—Average.

*Arrangement.*—Odd pinnate.

*Venation.*—Reticulate.

*Glossiness.*—Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal062', substantially as illustrated and described herein, due to its abundant medium red flowers, disease resistance, and extended period of bloom.

* * * * *

'Poulpal062'

'Poulpal062'